United States Patent [19]

Hoevel

[11] Patent Number: 4,655,716
[45] Date of Patent: Apr. 7, 1987

[54] CONTOURED MAMMOGRAPHY PHANTOM WITH SKIN

[75] Inventor: Marilyn K. Hoevel, Monrovia, Calif.

[73] Assignee: Xerox Corporation, Stamford, Conn.

[21] Appl. No.: 771,330

[22] Filed: Aug. 30, 1985

[51] Int. Cl.[4] ............................................. G09B 23/30
[52] U.S. Cl. ...................................... 434/267; 378/18
[58] Field of Search ................... 378/18, 207; 434/218, 434/267, 272, 273, 262, 263

[56] References Cited

U.S. PATENT DOCUMENTS

| | | | |
|---|---|---|---|
| 2,095,511 | 10/1937 | Oberto | 434/264 |
| 3,722,108 | 3/1973 | Chase | 434/267 |
| 3,867,638 | 2/1975 | Golden | 378/207 X |
| 3,963,933 | 6/1976 | Henkes | 378/18 X |
| 4,419,577 | 12/1983 | Guth | 378/207 X |

Primary Examiner—Harland S. Skogquist
Attorney, Agent, or Firm—Robert E. Cunha

[57] ABSTRACT

A phantom formed of a non-biological material into the shape of a breast, said material having radiation characteristics of breast tissue, for use by medical personnel while in training to interpret mammographs, and as a tool to assess the quality of a radiological imaging system. The phantom material comprises one epoxy resin based tissue substitute which simulates the breast tissue, and another which simulates the skin tissue. A slot is formed in the phantom into which targets for simulating breast masses, fibers and calcifications can be placed.

2 Claims, 3 Drawing Figures

CONTOURED MAMMOGRAPHY PHANTOM WITH SKIN

BACKGROUND OF THE INVENTION

This invention is a model of the human breast specifically formulated to simulate its x ray properties, and more specifically contains two separate materials to simulate the skin and underlying tissue.

Mammography phantoms are used as quality control test objects to evaluate x ray imaging systems. Phantoms are also used in various research and educational applications.

A major problem with phantoms is that they are made of materials which do not simulate the radiographic properties of breast tissue. A typical phantom is fabricated of a material scaled in size to match a single radiographic property of the modeled tissue, that is, linear attenuation. Sizing in this manner produces a limited purpose phantom and a poor representation of a breast. What is required is a phantom that will produce a more realistic x ray image of a breast and of its common anomalies such as masses, fibers and calcifications, so that an operator in training need not develop one set of mental images for the test object and another for actual breasts.

SUMMARY OF THE INVENTION

By using tissue equivalent materials, breast tissue and skin tissue, a realistic phantom is presented. Comparable phantom-to-breast images are attained. It is noted that the skin is a unique feature of this breast phantom. This model is fabricated from materials with physical radiation characteristics of breast tissue and skin tissue and is realistically contoured. Therefore, for medical personnel using this phantom while in training to interpret mammographs, the mental sets for the interpretation of the test article and the later interpretation of real x ray images are made using the same criteria.

Incorporated into the phantom is a target slot accepting random targets. The targets simulate common breast structures and anomalies associated with breast disease and cancer. Varying degrees of imagability are represented by graduated target arrays.

The epoxy resin based tissue substitutes used were formulated by D. R. White at St. Bartholomew's Hospital (White, D. R., Martin R. J., Parlson, R., "Epoxy Resin Based Tissue Substitutes", *British Journal of Radiology*, 50, 814–821, 1977.) These tissue equivalent epoxies simulate radiographic properties of the representative tissue; mass attenuation, energy absorbtion coefficient, electron mass stopping powers and mass angular scattering power.

The following design parameters were selected for an ideal breast phantom and incorporated into the design. The target should be fabricated from a non-biological tissue equivalent; it should appear in an x ray image similar to objects imaged in real breasts; subtle targets should be matched in opacity; target sizes should be graduated from obviously visible to not possible to image; targets should be able to be randomly placed; the phantom should have a shape that is realistic in contour and size as compared to an actual breast positioned for mammography; and the actual breast structure should be simulated.

DESCRIPTION OF THE PREFERRED EMBODIMENT

The contoured mammography phantom is shaped to represent an average sized breast slightly compressed in the caudal position for mammographic examination. Phantom dimensions are as follows:

Maximum thickness—4.6 cm (1.81 in.)
Maximum width—16.7 cm (6.57 in.)
Depth including nipple—10.5 cm (4.13 in.)
Skin thickness—1.5 cm (0.06 in.)
Target depth—1.5 cm (0.59 in.)

Figure 1:
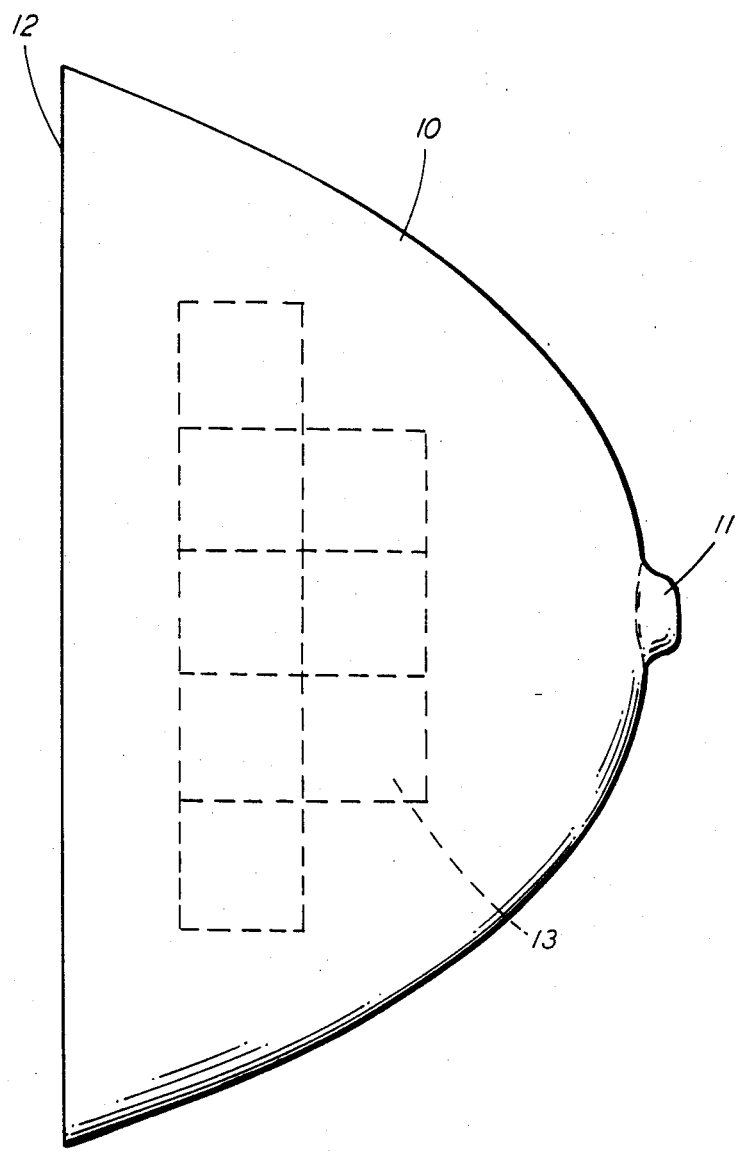
FIG. 1 is a representation of a radiograph of the phantom.

A representation of a xeroradiograph, FIG. 1, illustrates the phantom. Visible in the figure is the skin 10 which is unique to mammography phantoms. The skin material is also formed into a thickened portion 11 to simulate the nipple.

The skin is cast of SK-1, a skin equivalent epoxy modeled after the chemical composition of skin as published by the ICRP, 1975. The interior portion 12 of the breast phantom is BR-12, which is a breast tissue equivalent epoxy modeled as a homogenous mass of 50% adipose tissue and 50% water, closely approximating 50% adipose tissue and 50% glandular tissue. BR-12 is cast directly into the cured skin.

The epoxy resin is made up with a relatively high percentage (approximately 20%) of fillers or powders which modify its physical properties. One filler comprises phenolic microballoons to reduce the density. The microballoons are very small plastic spheres filled with inert gas. Another additive is polyethylene powder which helps to suspend the heavier, higher atomic number compounds, namely the aluminum fluoride in the skin material and the calcium carbonate in the equivalent breast tissue. By the use of this additive, the heavier components are not permitted to settle toward the bottom of the mold.

Without precautions being taken, the mixing of the various components would result in the creation of air bubbles in the mixture. Bubbles of up to four millimeters are common, affect the x ray beam characteristics, and be seen easily in a xeroradiograph. This is undesirable since the resultant x ray image will not resemble real breast tissue.

The epoxy and hardener as delivered are almost completely free of air bubbles. Therefore, any time two ingredients are mixed, this mixing step can be done in a vacuum chamber to prevent the formation of bubbles. In the alternative, the mixing can be done in air, and the mixture placed in a vacuum to withdraw the air bubbles. However, this procedure is not convenient since the epoxy is extremely viscous, and will expand to an unmanageable volume within the vacuum chamber.

The pot life of the epoxy is eight hours, and is cured after sixteen hours at room temperature and another six hours at 150¼F. (65¼C.).

The molds are made by first making a three dimensional model of a breast as it would be compressed for x ray viewing. From the model, an outer and then an inner mold can be made from epoxy, silicone or any other convenient material. A layer the thickness of skin is removed from the inner mold. Then, to make the skin, the correct amount of mixed epoxy is placed in the bottom of the outer mold, and the inner mold is inserted to extrude the material into shape. After curing and removal of the inner mold, the skin can be used as the mold for the remainder of the breast tissue. Finally, a ¼", (0.635 cm) Teflon plate is inserted in the breast tissue epoxy while it is still liquid to create a void for the insertion of test targets.

Figure 2A:
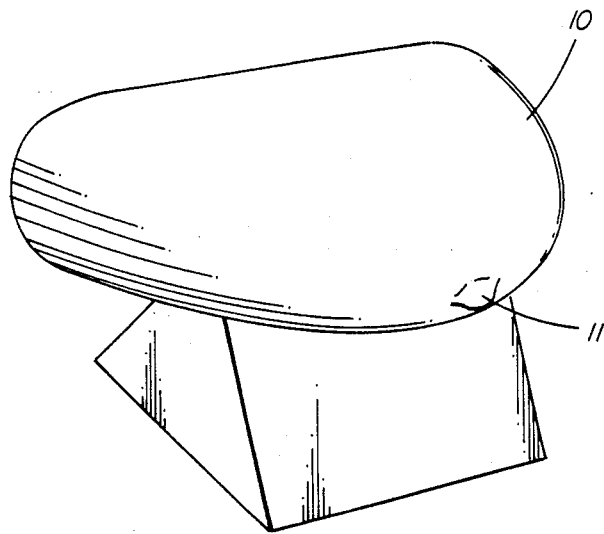
FIGS. 2A and 2B are front and back views of the phantom.
Figure 2B:
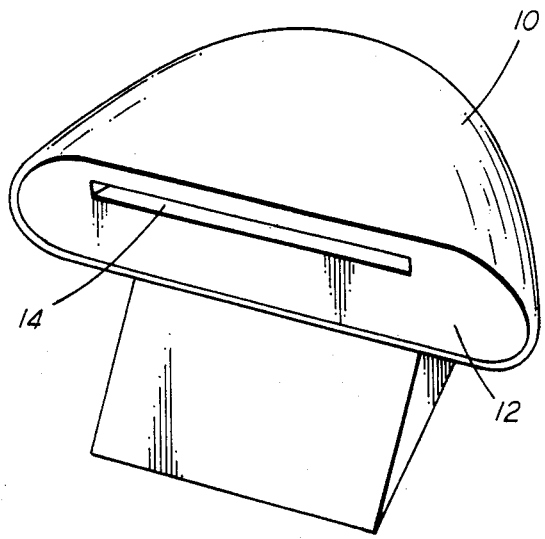

The contoured phantom is designed for random target 13 placement, a molded target slot 14 accepts eight ¾" (1.905 cm) by ¾" (1.905 cm) by ¼" (0.635 cm) targets. Target placement is 1.5 cm (0.59 in.) below the top of the phantom. This is shown in FIGS. 2A and 2B.

Along with the breast model itself, there is a need for targets of relevance to mammography. Predominantly, targets in mammography phantoms simulate masses, fibers and calcifications. Table A lists common phantoms commercially available and one-of-a-kind research test objects with target materials and sizes. Important is the material the target is embedded in, as this produces the relative contrast. Targets fabricated for the contoured phantom are listed for reference in Table B. All targets are potted in BR-12.

There is very little information on the chemical composition of cancerous masses or calcifications. In a study by Gaulkin (Gaulkin, B. M., Frasca, P., Feig, S. A., Holderness, K. E., "Non-Calcified Breast Particles, A Possible New Marker of Breast Cancer", Investigative Radiology, Vol. 17:2, pp. 119–128 Mar.-Apr., 1982), it was reported that many breast particles contain little or no calcium. Some breast particles contained only a single element. Metals were commonly found elements. Three materials were selected to represent breast calcifications: silicon, white saphire and aluminum. One objective was to fabricate calcification targets which were as difficult to image and as descriptive as breast particles indicative of cancer. D. W. Miller (Miller, D. W., Masterson, M. E., "Mammography Phantom Development at the Northeastern Center for Radiological Physics", Reduced Dose Mammography, Edited: Logan & Muntz, Masson Publishing USA, Inc. 1979), reported silicon to be radiographically representative of an average breast calcification.

Silicon chips presented in clusters provide an effective representation of calcifications. Silicon produces descriptive breast particles but a very subjective target.

Ultra fine aluminum wire with diameters of 0.004" (0.01 cm), 0.008" (0.02 cm) and 0.012" (0.03 cm), cut in lengths of 0.031" (0.0787 cm) to 0.125" (0.3175 cm) provide a representation of a linear type calcification. Since the material is commercially available and accurately sized, graduated targets are easily produced.

Aluminum oxide particles are used in several mammographic phantoms, as shown in Table A. These are generally irregular shaped specks or flakes which result in sizing inconsistency and degrades the target quality. To avoid this problem, industrial white sapphire balls, a form of aluminum oxide, were used. Sapphire balls are commercially available, accurately sized and inexpensive.

Two useful targets are sapphire balls with 0.016" (0.04 cm) and 0.032" (0.08 cm) diameters. The 0.032" (0.08 cm) target is too large, but 016" (0.04 cm) is effective at representing small punctate calcifications. Smaller sizes are required to provide a quantitive array of targets.

The design intent of targets representing fibers is to show relative contrast and fine structure detail. Fibers in the breast are predominantly caused by the contrast in density between glandular structures and adipose tissue. To represent fibers, small diameter rods of MS-11, a muscle equivalent epoxy, was used. The relative contrast between BR-12 and MS-11, the breast tissue and the muscle tissue epoxies, respectively, is somewhat lower (20%) than that of gland vs. adipose. This produces a low contrast target of relative radiographic significance to mammography.

Two other materials were used for targets, strands of fiberglass and hot melt glue. Fiberglass targets provide varying degrees of subtlety dependent on quality and shape. As with the aluminum phantom, fiberglass provides a subjective comparison for imageability of fine fibers. Targets comprising strands of hot melt glue are used primarily because of the ability to be easily formed. The resulting target is difficult to see as its low opacity is not expected. These low contrast fibers are of suspect relevance to mammmography.

Masses were fabricated of water equivalent epoxy, representative of cysts in the breast. The masses are wafer shaped disks. All edges have full radii to avoid edge enhancement induced visibility and to maintain low contrast. The detectability of mass targets depends primarily on the thickness. Targets ranging from clearly visible to invisible are provided with the mass thickness ranging from 0.063" (0.16 cm) to 0.016" (0.04 cm).

The preferred targets are the tissue equivalent rods, sapphire balls and water equivalent masses.

The non-biological materials mentioned above for both the breast tissue and the skin tissue are manufacturable and suitable for producing the large castings required for mammography phantom.

While the invention has been described with reference to a specific embodiment, it will be understood by those skilled in the art that various changes may be made and equivalents may be substituted for elements thereof without departing from the true spirit and scope of the invention. In addition, many modifications may be made without departing from the essential teachings of the invention.

What is claimed is:

1. A breast phantom comprising:
    a first non-biological tissue substitute having radiographic properties of breast tissue, shaped in the size and contour of an actual breast slightly flattened and positioned for a mammograph, and
    a second non-biological tissue substitute having radiographic properties of skin tissue, of a thickness representative of the skin of a breast, covering said first tissue substitute, and
    wherein, within said first tissue substitute is formed a target slot into which targets for simulating various sizes, shapes and types of breast masses, fibers and calcifications can be placed.

2. The phantom of claim 1 wherein said tissue substitutes are epoxy resin based.

* * * * *